United States Patent
Lou et al.

(10) Patent No.: US 8,436,155 B2
(45) Date of Patent: May 7, 2013

(54) 7,2"-DEHYDRATE PUERARIN AND ITS SALTS, PREPARATION METHOD AND USE THEREOF

(75) Inventors: Hongxiang Lou, JiNan (CN); Jian Gao, JiNan (CN); Xia Xue, JiNan (CN)

(73) Assignee: Shandong University, Jinan (CN)

( * ) Notice: Subject to any disclaimer, the term of this patent is extended or adjusted under 35 U.S.C. 154(b) by 63 days.

(21) Appl. No.: 13/177,575

(22) Filed: Jul. 7, 2011

(65) Prior Publication Data

US 2011/0269701 A1    Nov. 3, 2011

Related U.S. Application Data

(63) Continuation of application No. PCT/CN2010/000691, filed on May 17, 2010.

(30) Foreign Application Priority Data

Apr. 29, 2010   (CN) .......................... 2010 1 0159299

(51) Int. Cl.
- *C07H 15/00* (2006.01)
- *C07H 17/00* (2006.01)
- *C07H 17/02* (2006.01)
- *C07H 15/04* (2006.01)
- *C07H 1/00* (2006.01)
- *C07H 3/00* (2006.01)

(52) U.S. Cl.
USPC ............. 536/8; 536/17.9; 536/18.5; 536/120; 536/124

(58) Field of Classification Search ........................ None
See application file for complete search history.

(56) References Cited

U.S. PATENT DOCUMENTS 7,727,965 B2 *   6/2010   Wang et al. ..................... 514/23

* cited by examiner

*Primary Examiner* — Traviss C McIntosh, III

(74) *Attorney, Agent, or Firm* — Matthias Scholl P.C.; Matthias Scholl

(57) ABSTRACT

A 7,2"-dehydrate puerarin represented by formula (I) and salt derivatives thereof. The compounds are prepared from puerarin by intramolecular mitsunobu reaction. They are capable of shortening arrhythmia duration and prolonging coagulation time. They can be prepared into oral formulations or injections for treatment of cardiovascular and cerebrovascular diseases including arrhythmia, coronary heart disease, angina pectoris, myocardial infarction, and cerebral infarction.

6 Claims, 8 Drawing Sheets

7,2"-DEHYDRATE PUERARIN AND ITS SALTS, PREPARATION METHOD AND USE THEREOF

CROSS-REFERENCE TO RELATED APPLICATIONS

This application is a continuation of International Patent Application No. PCT/CN2010/000691 with an international filing date of May 17, 2010, designating the United States, now pending, and further claims priority benefits to Chinese Patent Application No. 201010159299.7 filed Apr. 29, 2010. The contents of all of the aforementioned applications, including any intervening amendments thereto, are incorporated herein by reference.

BACKGROUND OF THE INVENTION

1. Field of the Invention

The invention relates to a puerarin derivative and preparation method and use thereof, and more particularly to a 7,2"-dehydrate puerarin and its salts, as well as to preparation method, and use thereof.

2. Description of the Related Art

Puerarin is an isoflavone glycoside extracted from roots of such legumes as kudzu and *Pueraria thomsonii*. Studies have shown that puerarin can eliminate free radicals, reduce serum cholesterol, and resist against coagulation and allergy. In clinic, puerarin is used for treatment of coronary heart diseases, angina pectoris, myocardial infarction, sudden deafness, and alcoholism.

With so many above-mentioned pharmacological activities, puerarin and derivatives thereof have aroused more and more attention. However, oral administration of puerarin has poor absorption and bioavailability, thereby resulting in a limited application. A conventional dosage form of puerarin for clinical application is injections, but the solubility and bioavailability thereof still need to be improved. To achieve this, structural modification or special formulations of puerarin are being developed. For example, acetylated and triphenylmethylated puerarin significantly improves the blood flow of rabbit eyes. The water-solubility of glycosylated puerarin has been improved greatly. 7-acetylsalicylic acyl puerarin has significant dose-dependent inhibition ($IC_{50}$=0.91 mmol/L) on platelet aggregation in vitro, and the inhibition is obviously stronger than that achieved by equivalent amount of aspirin or puerarin.

Studies have shown that phenolic hydroxyl of C-glycosylflavones reacts with a hydroxyl of a glycosyl unit thereof intramolecularly to yield a dehydrated derivative with strong bioactivity. In the prior art, no 7,2"-dehydrate puerarin and derivatives thereof has been disclosed.

SUMMARY OF THE INVENTION

In view of the above-described problems, it is one objective of the invention to provide a puerarin derivative, that is, 7,2"-dehydrate puerarin and salt derivatives thereof as well as a method for producing the same, to solve the problems of low bioavailability of oral administration of puerarin and of single dosage form for clinical application.

It is another objective of the invention to provide a use of 7,2"-dehydrate puerarin and a salt derivative thereof for prevention and/or treatment of cardiovascular and cerebrovascular diseases comprising arrhythmia, coronary heart disease, angina pectoris, myocardial infarction, and cerebral infarction.

In accordance with one embodiment of the invention, provided is a 7,2"-dehydrate puerarin represented by formula (I),

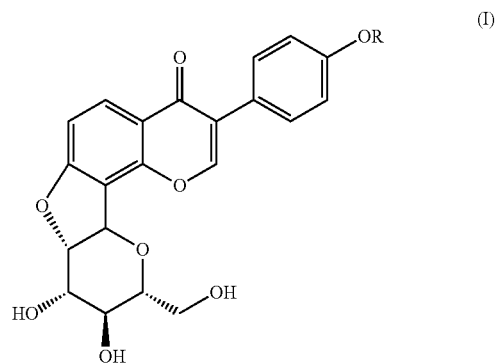

(I)

wherein R is H.

In accordance with another embodiment of the invention, provided is a salt derivative of 7,2"-dehydrate puerarin prepared by reacting 4'-position hydroxyl of 7,2"-dehydrate puerarin with an organic or inorganic base. After the reaction, R is $Na^+$, $K^+$, or

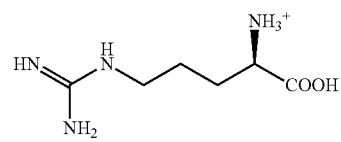 [SMILES: N=C(N)NCCC[C@@H]([NH3+])C(=O)O]

A method for producing 7,2"-dehydrate puerarin comprises a) in the presence of an organic solvent, mixing puerarin, $PY_3$, and an azo compound in a molar ratio of 1:(1-4):(1-4) to initiate an intramolecular Mitsunobu reaction to yield a compound represented by formula (I); and b) filtering, concentrating, applying silica gel column chromatography, separating, and purifying the compound; wherein Y in $PY_3$ is an aryl, alkyl, heteroaryl, or alkoxy. The synthetic reaction is summarized below:

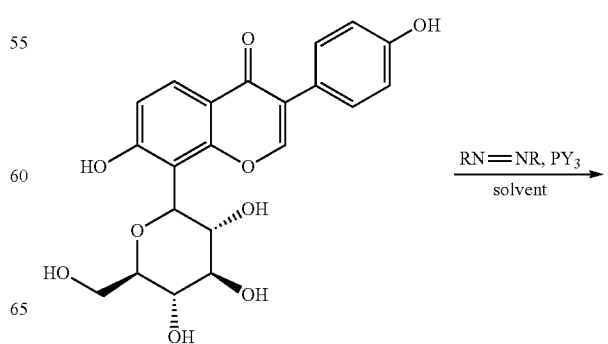

-continued

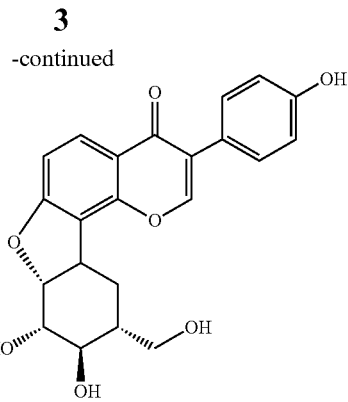

In a class of this embodiment, the azo compound is diisopropyl azodicarboxylate (DIAD), diethyl azodicarboxylate (DEAD); N,N,N', N'-tetramethyl azodicarbonamide (TMAD), or azodicarboxylic acid dipiperidide (ADDP).

In a class of this embodiment, the organic solvent is tetrahydrofuran, dioxane, methylene chloride, chloroform, dimethylformamide, toluene, benzene, or hexamethylphosphoramide.

Reacting 4'-position hydroxyl (having weak acidity) of 7,2"-dehydrate puerarin with an organic or inorganic base to yield the salt derivative of 7,2"-dehydrate puerarin has improved the water-solubility and stability and pharmacokinetic parameters thereof.

7,2"-dehydrate puerarin and a salt derivative thereof are used as a medicament for prevention and/or treatment of cardiovascular and cerebrovascular diseases comprising arrhythmia, coronary heart disease, angina pectoris, myocardial infarction, and cerebral infarction.

The medicament comprising 7,2"-dehydrate puerarin or a salt derivative thereof is administered in any pharmaceutically acceptable dosage form, particularly oral preparations or injections.

Studies have shown that phenolic hydroxyl of C-glycosylflavones reacts with a hydroxyl of a glycosyl unit thereof intramolecularly to yield a dehydrated derivative with strong bioactivity. Puerarin is an isoflavone c-glycoside with 4'-position hydroxyl having weak acidity as an active group. As mother nucleus isoflavone is a planar structure, 8-position glucopyranoside can be modified, i.e., an intramolecular mitsunobu reaction between 2"-position hydroxyl and 7-position hydroxyl to yield 7,2"-dehydrate puerarin.

Similar to puerarin, 7,2"-dehydrate puerarin has good prevention and treatment effect on cardiovascular and cerebrovascular diseases comprising arrhythmia, coronary heart disease, angina pectoris, myocardial infarction, and cerebral infarction, and studies show that the part of activity of the former is significantly stronger than that of the latter. 7,2"-dehydrate puerarin alters the polarity and dimensional structure of puerarin, thereby improving the water-solubility and cell membrane permeability of medicaments, enhancing the assimilation in the gastrointestinal tract, and improving the oral bioavailability of puerarin. Thus, the compound has a bright prospect for prevention and treatment of cardiovascular and cerebrovascular diseases.

Note: Each of FIGS. 1-6 comprises three sections, i.e., an ECG obtained exactly upon administering 0.1% $BaCl_2$, an arrhythmia ECG obtained after administration of 0.1% $BaCl_2$, and an ECG obtained at 30 min after administration of 0.1% $BaCl_2$.

DETAILED DESCRIPTION OF THE EMBODIMENTS

For further illustrating the invention, experiments detailing a 7,2"-dehydrate puerarin and salt derivative, preparation method, and use thereof are described below. It should be noted that the following examples are intended to describe and not to limit the invention.

EXAMPLE 1

Preparation of 7,2"-Dehydrate Puerarin

In the presence of $N_2$, 2.9 g (about 7 mmol) of puerarin was dissolved in 200 mL of anhydrous tetrahydrofuran. The solution was placed in an ice bath, to which 3.5 mL (about 17.5 mmol) of diisopropyl azodicarboxylate and 4.6 g (about 17.5 mmol) of triphenylphosphine were added. The mixture was heated gradually to room temperature, stirred magnetically for 16 hrs, concentrated, and performed with conventional silica gel column chromatography ($CH_2Cl_2$:$CH_3OH$=13:1, 8:1) to yield 2.4 g of 7,2"-dehydrate puerarin, with a yield of 87.1%.

7,2"-dehydrate puerarin is a white powder, with a molecular formula of $C_{21}H_{18}O_8$, a structural formula represented by formula (I)

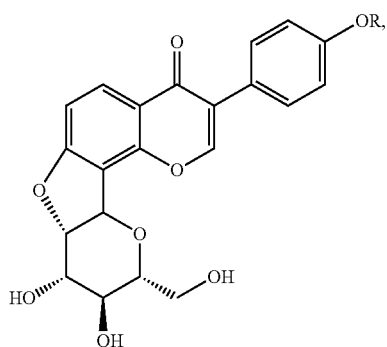

and molecular weight of 398, mp 258.4-260.1° C.; $^1H$ NMR (600 MHz, $CD_3OD$): δ 8.23 (d, 1H, J=8.4 Hz), 8.21 (s, 1H), 7.39 (d, 2H, J=8.4 Hz), 7.13 (d, 1H, J=8.4 Hz), 6.87 (d, 2H, J=8.4 Hz), 5.45 (d, 1H, J=3.6 Hz), 4.81 (t, 1H, J=3.6 Hz), 4.07

Figure 1:
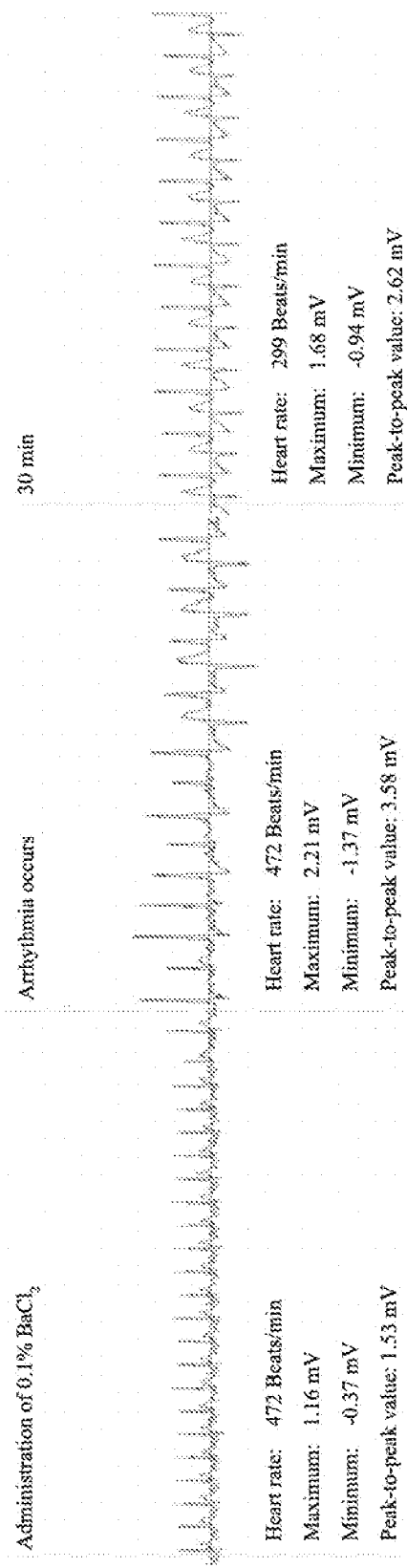
FIG. 1 is an ECG (Electrocardiogram) of a normal saline group according to one embodiment of the invention.
Figure 2:
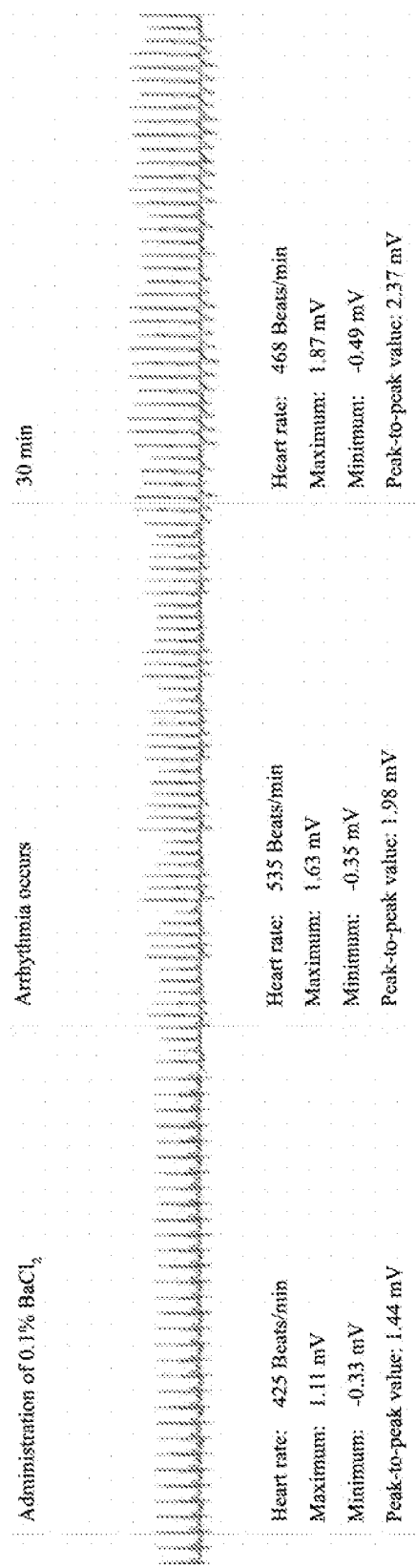
FIG. 2 is an ECG (Electrocardiogram) of a propylene glycol solvent gavage group according to one embodiment of the invention.
Figure 3:
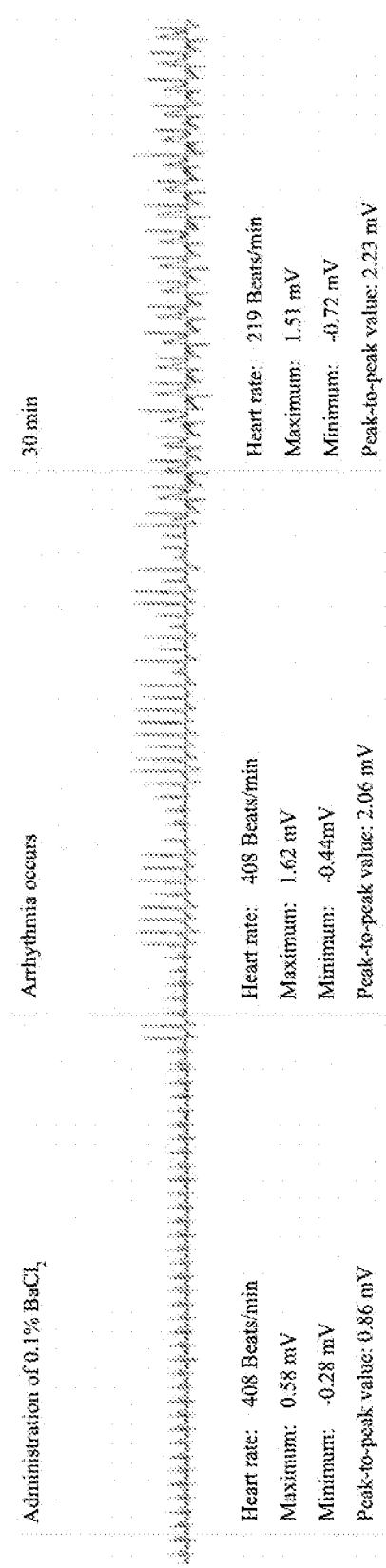
FIG. 3 is an ECG (Electrocardiogram) of a propylene glycol solvent intravenous injection group according to one embodiment of the invention.
Figure 4:
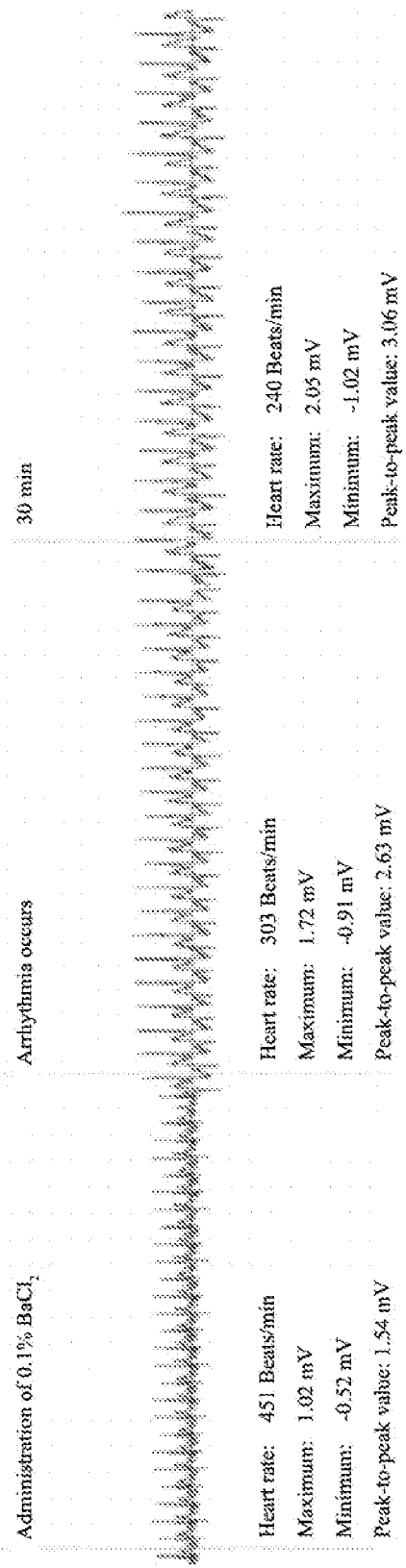
FIG. 4 is an ECG (Electrocardiogram) of a puerarin injection group according to one embodiment of the invention.
Figure 5:
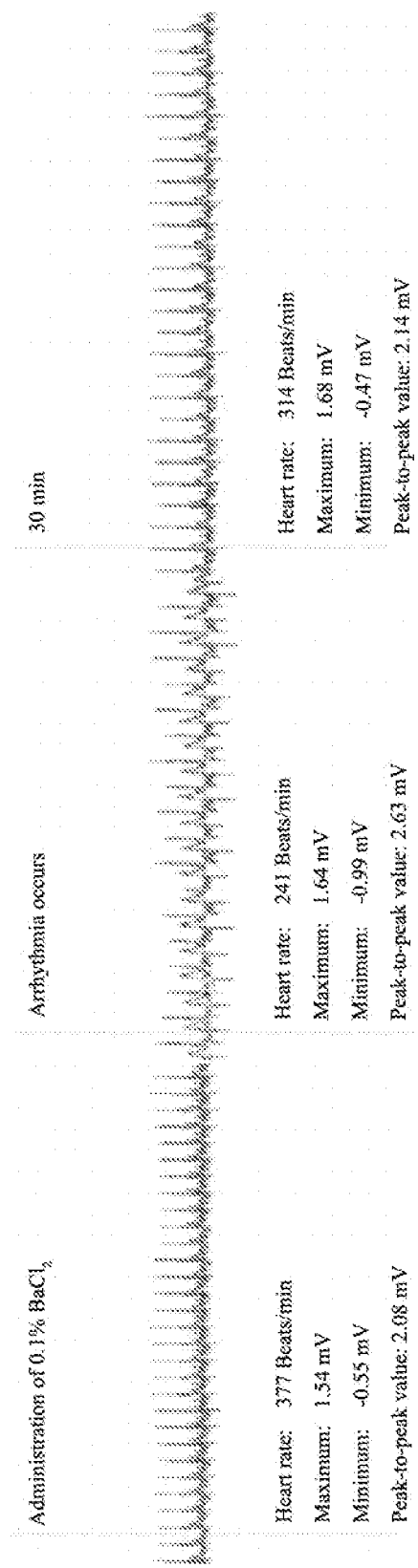
FIG. 5 is an ECG (Electrocardiogram) of a 7,2"-dehydrate puerarin gavage group according to one embodiment of the invention.
Figure 6:
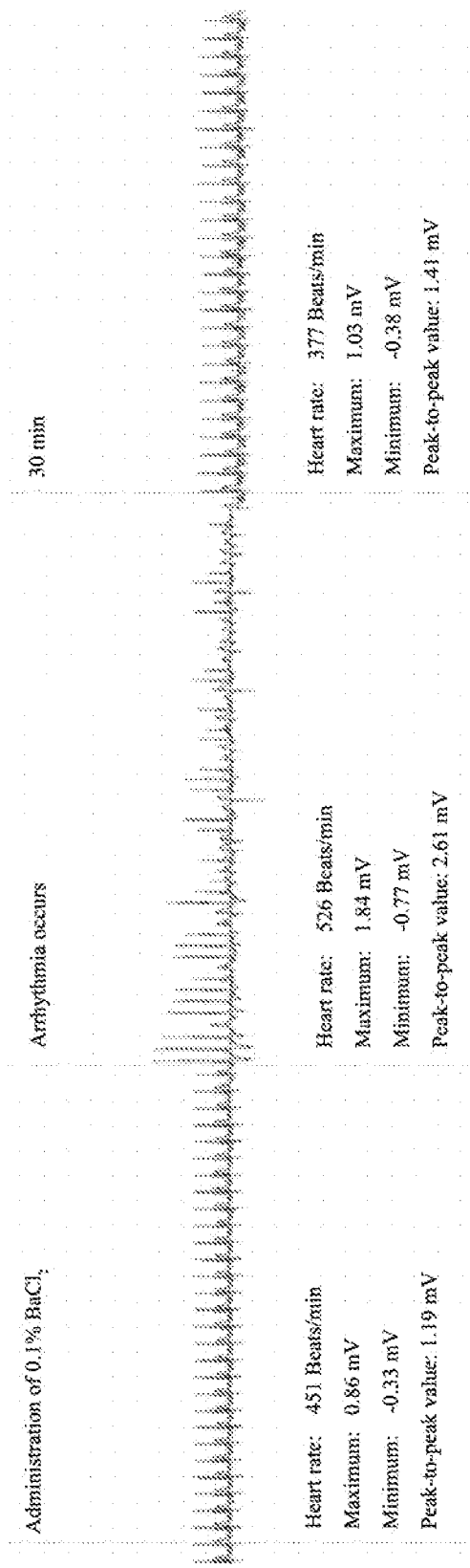
FIG. 6 is an ECG (Electrocardiogram) of a 7,2"-dehydrate puerarin intravenous injection group according to one embodiment of the invention.
Figure 7:
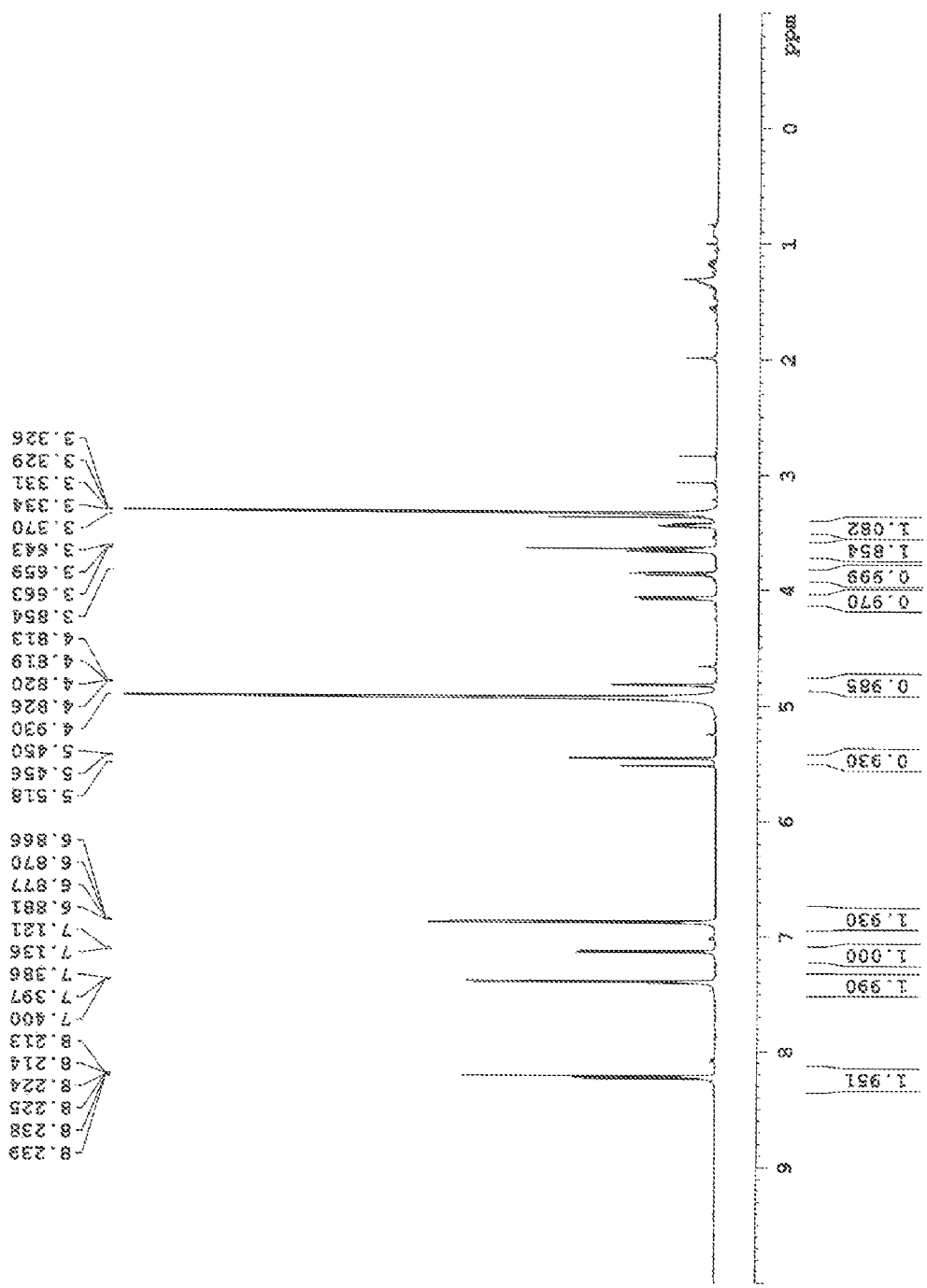
FIG. 7 is a graph of $^1H$ NMR of 7,2"-dehydrate puerarin according to one embodiment of the invention.
Figure 8:
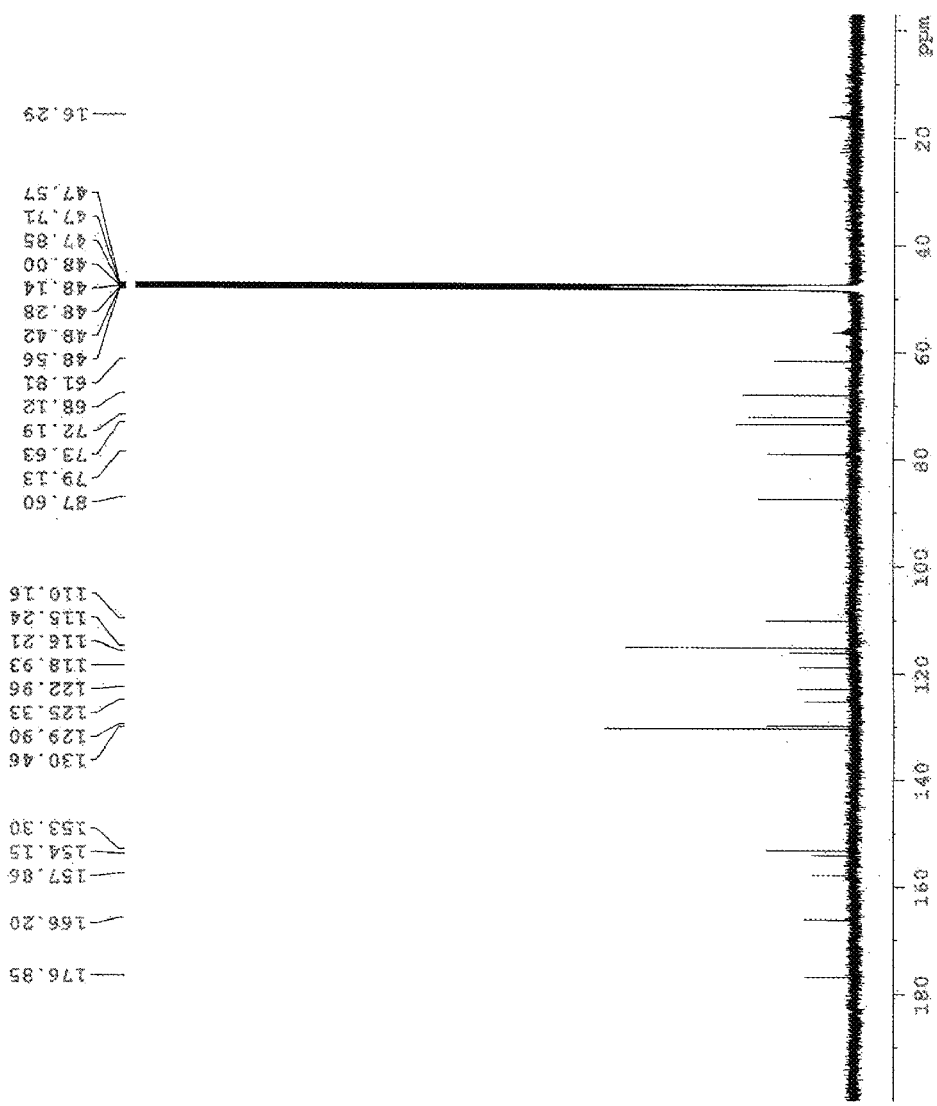
FIG. 8 is a graph of $^{13}C$ NMR of 7,2"-dehydrate puerarin according to one embodiment of the invention.

(dd, 1H, J=4.8, 9.6 Hz), 3.87 (dd, 1H, J=2.4, 12.0 Hz), 3.65 (m, 2H), 3.43 (m, 1H); $^{13}$C NMR (150 MHz, CD$_3$OD): δ 61.8, 68.1, 72.1, 73.6, 79.1, 87.6, 110.1, 115.2, 116.2, 118.9, 122.9, 125.3, 129.9, 130.4, 153.3, 154.1, 157.8, 166.2, 176.8; HRMS (ESI) m/z calcd for C$_{21}$H$_8$O$_8$[M+Na]$^+$ 421.0894, found 421.0893 (as shown in FIGS. 7 and 8).

EXAMPLE 2

Preparation of 7,2"-Dehydrate Puerarin

In the presence of N$_2$, 2.9 g (about 7 mmol) of puerarin was dissolved in 200 mL of anhydrous tetrahydrofuran. The solution was placed in an ice bath, to which 2.4 g (about 14.0 mmol) of N,N,N',N'-tetramethyl azodicarbonamide and 3.4 mL (about 14.0 mmol) of tri-butyl phosphate were added. The mixture was heated gradually to room temperature, stirred magnetically for 16 hrs, concentrated, and performed with conventional silica gel column chromatography (CH$_2$Cl$_2$:CH$_3$OH=13:1, 8:1) to yield 2.2 g of 7,2"-dehydrate puerarin, with a yield of 81.4%.

EXAMPLE 3

Preparation of 7,2"-Dehydrate Puerarin

In the presence of N$_2$, 2.9 g (about 7 mmol) of puerarin was dissolved in 200 mL of anhydrous tetrahydrofuran. The solution was placed in an ice bath, to which 1.6 g (about 10.5 mmol) of diethyl azodicarboxylate and 2.8 g (about 10.5 mmol) of triphenylphosphine were added. The mixture was heated gradually to room temperature, stirred magnetically for 16 hrs, concentrated, and performed with conventional silica gel column chromatography (CH$_2$Cl$_2$:CH$_3$OH=13:1, 8:1) to yield 2.1 g of 7,2"-dehydrate puerarin, with a yield of 77.5%.

EXAMPLE 4

Antiarrhythmic Experiments of 7,2"-Dehydrate Puerarin

1. Method: 60 male, healthy adult Wistar rats with body weight of 180-220 g were randomly divided into 6 groups, i.e., a normal saline group, a propylene glycol solvent gavage group, a propylene glycol solvent intravenous injection group, a puerarin injection group, a 7,2"-dehydrate puerarin gavage group, and a 7,2"-dehydrate puerarin intravenous injection group, with 10 rats each group. The intravenous injection was carried out one time a day for three consecutive days. The gavage was carried out two times a day for three consecutive days. The normal saline group was administered with equal volume of 0.9% NaCl injection. The dose of the propylene glycol solvent gavage group was 14.3% propylene glycol 1 mL/100 g. The dose of the propylene glycol solvent intravenous injection group was 40% propylene glycol 0.5 mL/100 g. The dose of the puerarin injection group was 50 mg/kg. The dose of the 7,2"-dehydrate puerarin gavage group was 60 mg/kg. The dose of the 7,2"-dehydrate puerarin intravenous injection group was 30 mg/kg. The rats were anesthetized with 10% chloral hydrate (0.35 mL/100 g) by intraperitoneal injection and fixed in the back. A BL-410 biological functional system was introduced to monitor the ECG changes of the rats. A femoral vein of the rats was exposed, a scalp needle inserted, and a constant speed syringe pump connected. 0.1% BaCl$_2$ was pumped with a dose of 0.1 mL/100 g and a speed of 0.6 mL/min. From the injection of BaCl$_2$ on, the ECGs were monitored and recorded within 30 min. The arrhythmia latency and arrhythmia duration were recorded (if not restored within 30 min, the record was 30 min). The experimental results were collected and analyzed using Software SPSS. If P<0.05, the results has significant difference.

2. Results: The ECGs were shown in FIGS. 1-6 and experimental data were listed in Table 1.

TABLE 1

Influence of 7,2"-dehydrate puerarin on rat arrhythmias ($\bar{x} \pm $ SD)

| Groups | Dose | Arrhythmia latency (s) | Arrhythmia duration (min) |
|---|---|---|---|
| Normal saline | NS | 21.50 ± 8.58 | 30 |
| Propylene glycol solvent gavage | 1.4 mL/kg | 39.75 ± 11.44 | 30 |
| Propylene glycol solvent intravenous injection | 2 mL/kg | 75.75 ± 20.35** | 30 |
| Puerarin injection | 50 mg/kg | 86.75 ± 42.55** | 30 |
| 7,2"-dehydrate puerarin gavage | 60 mg/kg | 29.25 ± 5.12$^{\#\#}$ | 2.09 ± 0.98**$^{\#\#}$ |
| 7,2"-dehydrate puerarin intravenous injection | 30 mg/kg | 47.25 ± 19.87$^{\#}$ | 17.75 ± 4.61**$^{\#}$ |

Note:
In contrast to the normal saline group,
*P < 0.05,
**P < 0.01;
in contrast to the puerarin injection group,
$^{\#}$P < 0.05,
$^{\#\#}$P < 0.01.

In contrast to the normal saline group, the 7,2"-dehydrate puerarin gavage group and the 7,2"-dehydrate puerarin intravenous injection group prolonged the arrhythmia latency reduced by 0.1% BaCl$_2$, but there is no statistical significance. In contrast to the normal saline group, the 7,2"-dehydrate puerarin gavage group and the 7,2"-dehydrate puerarin intravenous injection group significantly shortened the arrhythmia duration (**P<0.01). In contrast to the positive control group, i.e., the puerarin injection group, the 7,2"-dehydrate puerarin gavage group also significantly shortened the arrhythmia duration, with statistical significance (*P<0.05, **P<0.01). Furthermore, In contrast to the 7,2"-dehydrate puerarin intravenous injection group, the 7,2"-dehydrate puerarin gavage group significantly shortened the arrhythmia duration, with a better effect.

3. Conclusion: 7,2"-dehydrate puerarin and derivatives thereof can significantly shorten the arrhythmia duration, with high water-solubility and bioavailability.

EXAMPLE 5

Anticoagulation Experiments of 7,2"-Dehydrate Puerarin

1. Method: A rabbit was weighed and injected with 3% sodium pentobarbital 1 mL/kg via an ear vein, and then anaesthetized. A carotid artery of the rabbit was exposed, the distal end thereof was ligated and the proximal end was received by a catheter. 25 mL of blood was collected, added to a test tube containing 0.5 mL of 50 mg/mL potassium oxalate, and mixed to yield a uniform mixture. 24 small test tubes were collected, to which 0.25 mL of corresponding reagents were added, respectably. 0.9 mL of the above-mentioned mixture was added to each of the small test tubes, respectively, and then 0.1 mL of 2 mg/mL CaCl$_2$ was added. The resulting solution was shaken uniformly and put into a constant temperature water bath (37±0.5° C.). Every 30 seconds, the small test tubes were tilted slightly once, and the coagulation time was recorded (the test tubes were tilted slightly, if no blood bled, the time was recorded as coagulation time). The experimental results were collected and analyzed using Software SPSS. If P<0.05, the results has significant difference.

2. Results: As shown in Table 2,

TABLE 2

| Anticoagulation effect of 7,2"-dehydrate puerarin in vitro ($\bar{x} \pm SD$) | | |
|---|---|---|
| Groups | Concentration | coagulation time (min) |
| Normal saline | NS | 3.8 ± 0.4 |
| Propylene glycol solvent | 20% (v/v) | 11.7 ± 1.5** |
| Puerarin | 3 mg/mL | 15.3 ± 2.4**▲ |
| 7,2"-dehydrate puerarin (low dose) | 0.75 mg/mL | 14.7 ± 1.6** |
| 7,2"-dehydrate puerarin (medium dose) | 1.5 mg/mL | 22.7 ± 2.6**##▲▲ |
| 7,2"-dehydrate puerarin (high dose) | 3 mg/mL | 38.5 ± 2.1**##▲▲ |

Note:
In contrast to the normal saline group,
*P < 0.05,
**P < 0.01;
in contrast to the puerarin group,
P < 0.05,
P < 0.01;
in contrast to the propylene glycol solvent group,
▲P < 0.05,
▲▲P < 0.01.

In contrast to the normal saline group, the solvent group and reagent groups prolonged the coagulation time, and there is statistical difference. In contrast to the positive control group, i.e., the puerarin group, the 7,2"-dehydrate puerarin (high dose) group significantly prolonged the coagulation time, with a significant statistical difference (**P<0.01). In contrast to the propylene glycol solvent group, the 7,2"-dehydrate puerarin (high dose) group significantly prolonged the coagulation time, with a significant statistical difference (▲P<0.05, ▲▲P<0.01, ▲▲P<0.01).

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of formula (I), wherein R is H,

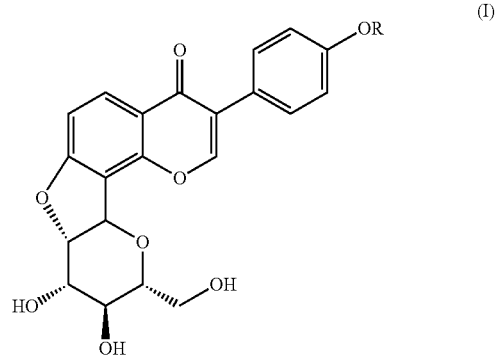

or a salt derivative thereof.

2. The compound of claim 1, wherein said salt derivative thereof is prepared by reacting 4'-position hydroxyl of 7,2"-dehydrate puerarin with an organic or inorganic base.

3. The compound of claim 2, wherein R is Na$^+$, K$^+$, or

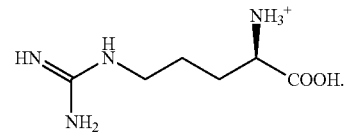 [SMILES: N=C(N)NCCC[C@@H]([NH3+])C(=O)O]

4. A method for producing the compound of claim 1, comprising:
   a) in the presence of an organic solvent, mixing puerarin, PY$_3$, and an azo compound in a molar ratio of 1:(1-4):(1-4) to initiate an intramolecular Mitsunobu reaction to yield a compound represented by formula (I); and
   b) filtering, concentrating, applying silica gel column chromatography, separating, and purifying the compound; wherein Y in PY$_3$ is an aryl, alkyl, heteroaryl, or alkoxy.

5. The method of claim 4, wherein said azo compound is diisopropyl azodicarboxylate, diethyl azodicarboxylate, N,N,N',N'-tetramethyl azodicarbonamide, or azodicarboxylic acid dipiperidide.

6. The method of claim 4, wherein said organic solvent is tetrahydrofuran, dioxane, methylene chloride, chloroform, dimethylformamide, toluene, benzene, or hexamethylphosphoramide.

* * * * *